(12) United States Patent
Das (10) Patent No.: US 12,216,054 B2
(45) Date of Patent: Feb. 4, 2025

(54) METHOD FOR MEASURING MONOCHLORAMINE WITH A THIOCARBAMATE INDICATOR AND BUFFER

(71) Applicant: HACH COMPANY, Loveland, CO (US)

(72) Inventor: Amit Das, Timnath, CO (US)

(73) Assignee: HACH COMPANY, Loveland, CO (US)

(*) Notice: Subject to any disclaimer, the term of this patent is extended or adjusted under 35 U.S.C. 154(b) by 349 days.

(21) Appl. No.: 17/070,113

(22) Filed: Oct. 14, 2020

(65) Prior Publication Data

US 2021/0025862 A1 Jan. 28, 2021

Related U.S. Application Data

(63) Continuation-in-part of application No. 16/411,855, filed on May 14, 2019, now Pat. No. 11,506,605.

(51) Int. Cl.
| | |
|---|---|
| G01N 21/64 | (2006.01) |
| G01N 21/77 | (2006.01) |
| G01N 31/22 | (2006.01) |
| G01N 33/18 | (2006.01) |
| C07D 311/16 | (2006.01) |

(52) U.S. Cl.
CPC ........... *G01N 21/643* (2013.01); *G01N 21/77* (2013.01); *G01N 31/22* (2013.01); *G01N 33/18* (2013.01); *C07D 311/16* (2013.01); *G01N 2021/6439* (2013.01); *G01N 2021/7786* (2013.01);

(Continued)

(58) Field of Classification Search
CPC ........... Y10T 436/173845; Y10T 436/193333; G01N 21/77; G01N 31/22; G01N 33/18; G01N 2021/6439; G01N 2021/7786
See application file for complete search history.

(56) References Cited

U.S. PATENT DOCUMENTS

| 2,278,053 A | 3/1942 | Behrman | |
| 11,422,093 B2 * | 8/2022 | Das | G01N 31/22 |

(Continued)

FOREIGN PATENT DOCUMENTS

CN 108409697 A 8/2018

OTHER PUBLICATIONS

Valentine, R.L. et al. "General Acid Catalysis of Monochloramine Disproportionation," Environ. Sel. Technol. 1988, 22, 691-696. (Year: 1988).*

(Continued)

*Primary Examiner* — Jennifer Wecker
*Assistant Examiner* — Michelle Adams
(74) *Attorney, Agent, or Firm* — Ference & Associates LLC (57) ABSTRACT

An embodiment provides a method for measuring total chlorine in a solution, including: preparing a thiocarbamate indicator; introducing the thiocarbamate indicator to a solution, wherein the solution contains an amount of monochloramine; adding an additive to the solution, wherein the additive accelerates the reaction rate between the thiocarbamate indicator and monochloramine and causes a change in fluorescence of the solution; and measuring the amount of monochloramine in the solution by measuring an intensity of the fluorescence. Other aspects are described and claimed.

8 Claims, 5 Drawing Sheets

(52) U.S. Cl.
CPC .............. *Y10T 436/173845* (2015.01); *Y10T 436/193333* (2015.01)

(56) References Cited

U.S. PATENT DOCUMENTS

| | | | |
|---|---|---|---|
| 11,549,888 B2 * | 1/2023 | Das | G01N 31/22 |
| 12,044,622 B2 * | 7/2024 | Das | G01N 21/643 |
| 2007/0114137 A1 | 5/2007 | Nomura et al. | |
| 2009/0320570 A1 * | 12/2009 | Wiese | G01N 33/182 73/61.43 |
| 2020/0363334 A1 * | 11/2020 | Das | G01N 21/643 |
| 2020/0386682 A1 * | 12/2020 | Das | G01N 21/643 |

OTHER PUBLICATIONS

Jafvert, C.T. et al. "Reaction Scheme for the Chlorination of Ammoniacal Water," Environ. Sci. Technol. 1992, 26, 577-586. (Year: 1992).*

Baocun Zhu et al., "A fast-response, highly specific fluorescent probe for the detection of picomolar hypochlorous acid and its bioimaging applications", Sensors and Actuators B: Chemical, 2018, 6 pages, Elsevier, B.V.

Xiao Wang et al., "A highly selective fluorescent probe for the detection of hypochlorous acid in tap water and living cells", Spectrochimica Acta Part A: Molecular and Biomolecular Spectroscopy, 2018, 15 pages, ScienceDirect.

Danial L. Harp, "Current Technology of Chlorine Analysis for Water and Wastewater", Technical Information Series—Booklet No. 17, 2002, 34 pages, Hach Company.

Hach Company, "Chlorine, Total (0 to 4.00 mg/L) For water, wastewater, and seawater", DOC316.53.01261, Method 10250, Mar. 2013, Edition 2, 8 pages, Hach Company.

Chinese Patent Office, Office Action on Chinese Patent Application No. 202080029176.3, Feb. 14, 2023, 20 pages, Chinese Patent Office.

Wang Yan et al., "Determinations of Free Chlorine and Chloramines in Dialysizing Water", Clinical Research, vol. 10, No. 11, pp. 588-593, Nov. 2011.

* cited by examiner

METHOD FOR MEASURING MONOCHLORAMINE WITH A THIOCARBAMATE INDICATOR AND BUFFER

BACKGROUND

This application relates generally to measuring chlorine in aqueous or liquid samples, and, more particularly, to the measurement of chlorine in low concentrations.

Ensuring water quality is critical in a number of industries such as pharmaceuticals and other manufacturing fields. Additionally, ensuring water quality is critical to the health and well-being of humans, animals, and plants which are reliant on the water for survival. One element that is typically measured is chlorine. Too much chlorine in water can be harmful to humans or animals, it can cause the water to have a bad taste or increased odor, and it can result in higher costs. Therefore, detecting the presence and concentration of chlorine in water or other liquid solutions is vital.

BRIEF SUMMARY

In summary, one embodiment provides a method for measuring total chlorine in a solution, comprising: preparing a thiocarbamate indicator; introducing the thiocarbamate indicator to a solution, wherein the solution contains an amount of monochloramine; adding an additive to the solution, wherein the additive accelerates the reaction rate between the thiocarbamate indicator and monochloramine and causes a change in fluorescence of the solution; and measuring the amount of monochloramine in the solution by measuring an intensity of the fluorescence.

Another embodiment provides a measurement device for measuring total chlorine in a solution, comprising: at least one measurement chamber; a processor; and a memory storing instructions executable by the processor to: prepare a thiocarbamate indicator; introduce the thiocarbamate indicator to a solution, wherein the solution contains an amount of monochloramine; add an additive to the solution, wherein the additive accelerates the reaction rate between the thiocarbamate indicator and monochloramine and causes a change in fluorescence of the solution; and measure a fluorescence intensity.

A further embodiment provides a method for measuring total chlorine in a solution, comprising: preparing a thiocarbamate indicator; introducing the thiocarbamate indicator to a solution, wherein the solution contains an amount of monochloramine; adding a buffer including citrate and phosphate to the solution, wherein the buffer adjusts the pH of the solution and accelerates the reaction rate between the thiocarbamate indicator and monochloramine and causes a change in fluorescence of the solution; and measuring the amount of monochloramine in the solution by measuring an intensity of the fluorescence.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional methods of chlorine measurement in water may have some limitations. For example, chlorine measurement may be used to determine the quality of water. High concentrations of chlorine may be harmful to animals, humans, and/or plants. Accordingly, as another example, a user or entity may want the chlorine in a body of water to be under a particular threshold, therefore, the user may measure the chlorine in order to determine if the amount of chlorine is under that threshold.

A standard for free and total chlorine measurement in water is DPD (N,N-diethyl-p-phenylenediamine) colorimetric detection. Total chlorine is the total amount of chlorine in the water including the chlorine that has reacted with nitrogen compounds in the water. In the absence of iodide ion, free chlorine reacts quickly with DPD indicator to produce a red color, whereas chloramines react more slowly. If a small amount of iodide ion is added, chloramines also react to produce color, yielding total chlorine concentration. Absorbance (for example, at 515 nm) may be spectrophotometrically measured and compared to a series of standards, using a graph or a regression analysis calculation to determine free and/or total chlorine concentration.

As set forth above, free chlorine reacts very quickly with DPD while the chloramine species (for example, monochloramine and dichloramine) react more slowly. In attempting to measure free chlorine, the presence of "interfering"

species such as monochloramine may produce inaccurate readings. For greatest accuracy, it is typically recommended that the free chlorine measurement using DPD should be made quickly (that is, before the interfering species can react to any significant degree).

Current methods, systems and kits for free chlorine measurement using the DPD colorimetric test are limited because the presence of chloramines can introduce significant errors in free chlorine measurements. Once again, if additional reagents are used to prevent interferences, then additional steps and/or toxic and expensive chemicals are required. Further, the traditional DPD colorimetric test does not allow monochloramine concentrations to be measured directly.

Accordingly, an embodiment provides a system and method for measuring chlorine at ultra low range (ULR) concentrations. In an embodiment, the method may not use traditional DPD chemistry. In an embodiment, the method may detect chlorine in concentrations below 20 parts per billion (ppb), and may yield accurate concentrations as low or lower than 2 ppb. In an embodiment, the method may use a fluorometric method. The indicator to give a fluorescent signal may be a thiocarbamate derivative. The thiocarbamate derivative may be a derivative of hydroxy coumarin. The thiocarbamate may be an umbelliferone thiocarbamate. The thiocarbamate derivative may include 7-hydroxy-coumarin and/or 7-hydroxy-4-methylcoumarin. An additive may be added in the method. The additive may accelerate the completion time of a reaction. The additive may include a buffer such as phosphate or citrate, or mixtures thereof. The additive may include potassium iodide (KI). In an embodiment, the fluorescence may be correlated to ULR detection of monochloramine. In an embodiment, the pH of a solution may be adjusted to activate the reporter or indicator molecule.

The illustrated example embodiments will be best understood by reference to the figures. The following description is intended only by way of example, and simply illustrates certain example embodiments.

Figure 1:
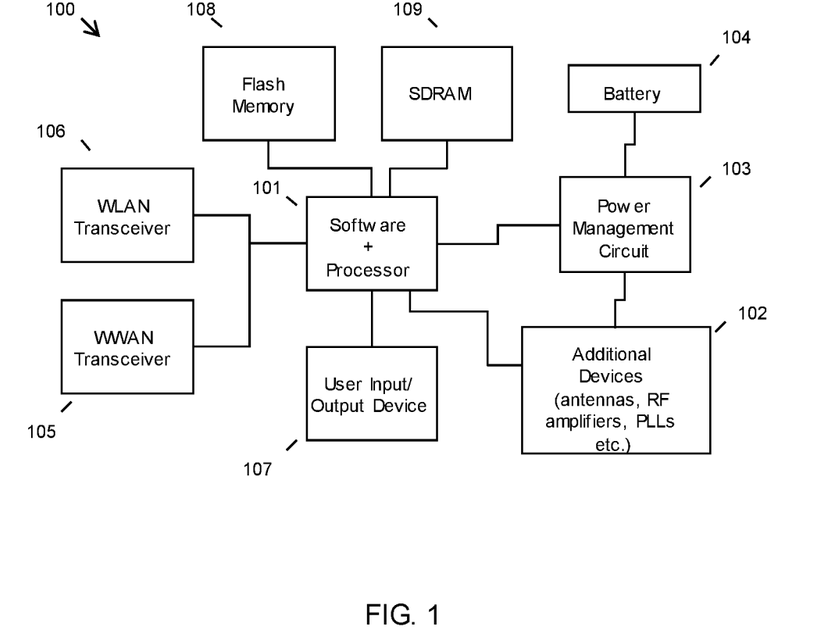
FIG. 1 illustrates an example of computer circuitry.

While various other circuits, circuitry or components may be utilized in information handling devices, with regard to an instrument for measurement of chlorine according to any one of the various embodiments described herein, an example is illustrated in FIG. 1. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 101. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of chlorine of an aqueous sample.

Figure 2:
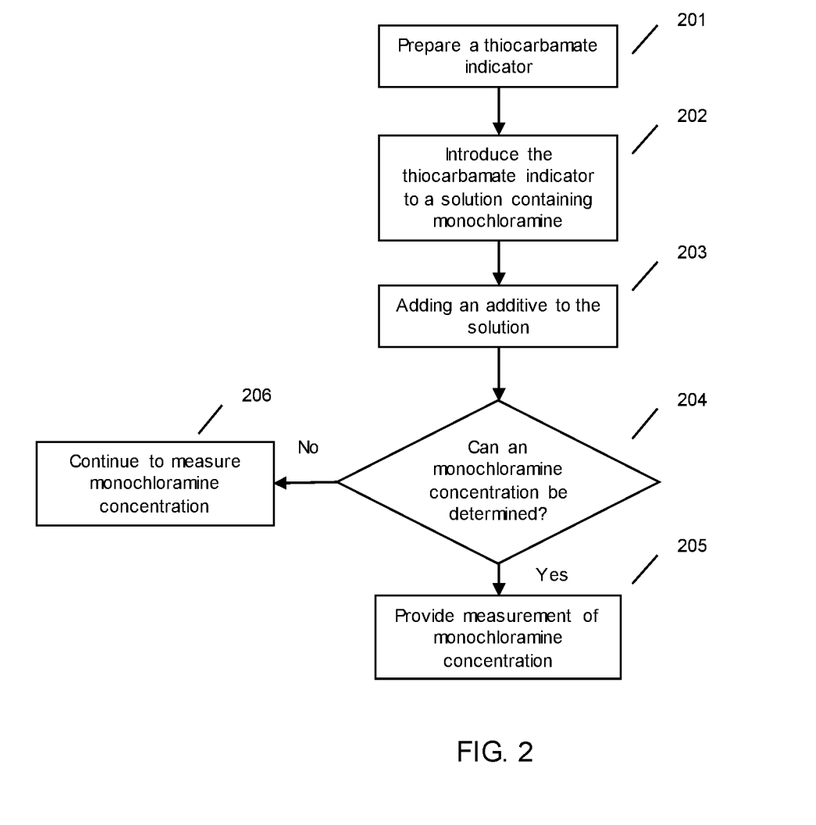
FIG. 2 illustrates a flow diagram of an example monochloramine measuring system.

Referring to FIG. 2, an example system and method for detection of monochloramine in solution is illustrated. In an embodiment, a thiocarbamate indicator may be prepared. The thiocarbamate indicator may be introduced to a solution containing monochloramine. In an embodiment, an additive may be added. The additive may include a buffer such as a phosphate or a citrate or mixture thereof. The additive may include potassium iodide. The additive may accelerate a reaction in solution. In an embodiment, the thiocarbamate indicator in the presence of monochloramine may cause a change in fluorescence intensity of the thiocarbamate indicator. The change of fluorescent intensity may be correlated to a concentration of monochloramine in the solution.

Figure 3:
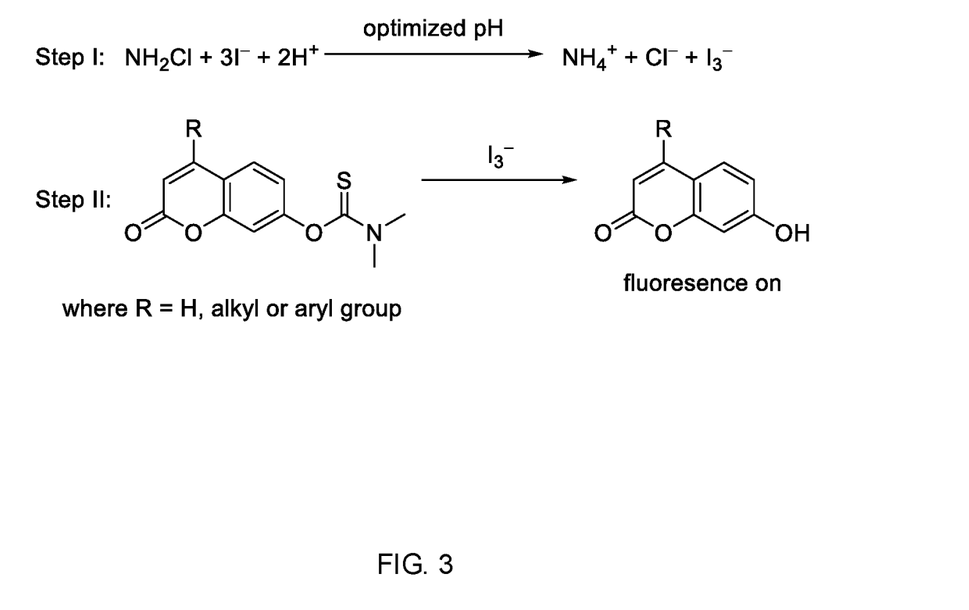
FIG. 3 illustrates a first chemical equation of an example thiocarbamate indicator for detection of monochloramine.
Figure 4:
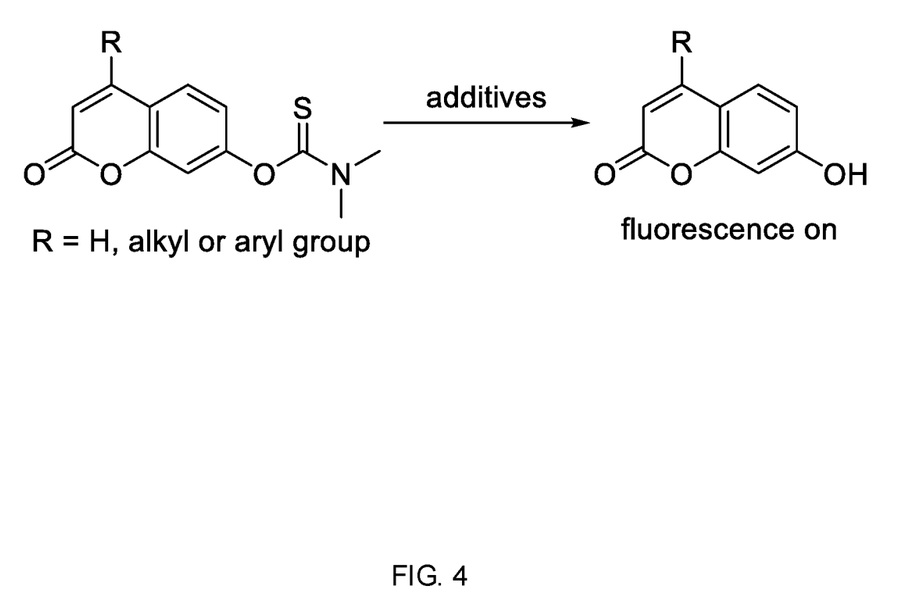
FIG. 4 illustrates a second chemical equation of an example thiocarbamate indicator for detection of monochloramine.

At 201, in an embodiment, a thiocarbamate indicator may be prepared. The thiocarbamate may be a thiocarbamate derivative of hydroxy coumarin. In an embodiment, the thiocarbamate indicator may be methylumbelliferone thiocarbamate or umbelliferone thiocarbamate. The thiocarbamate derivative may include 7-hydroxy-coumarin, 7-hydroxy-4-methylcoumarin, or mixtures thereof. Referring to FIG. 3, a first example reaction of the thiocarbamate indicator is illustrated. Referring to FIG. 4, a second example reaction of the thiocarbamate indicator is illustrated. In an embodiment, the thiocarbamate indicator may detect monochloramine in the ultra low range of less than 2 ppb.

At 202, in an embodiment, the thiocarbamate indicator may be introduced into a solution. The solution may contain monochloramine. The solution may be an aqueous sample which may include a sample from a natural body of water, a holding tank, a processing tank, a pipe, or the like. The solution may be in a continuous flow, a standing volume of liquid, or any combination thereof. In one embodiment, the solution may be introduced to the thiocarbamate indicator, for example, a test chamber of the measurement device. Introduction of the solution into the measurement device may include placing or introducing the solution into a test chamber manually by a user or using a mechanical means, for example, gravity flow, a pump, pressure, fluid flow, or the like. For example, a water sample for chlorine testing may be introduced to a measurement or test chamber using a pump. In an embodiment, valves or the like may control the influx and efflux of the solution into or out of the one or more chambers, if present.

Additionally or alternatively, the measurement device may be present or introduced in a volume of the solution.

The measurement device is then exposed to the volume of solution where it can perform measurements. The system may be a flow-through system in which a solution and/or reagents are automatically mixed and measured. Once the sample is in contact with the measurement system, the system may measure the chlorine of the sample, as discussed in further detail herein. In an embodiment, the measurement device may include one or more chambers in which the one or more method steps may be performed.

At 203, in an embodiment, an additive may be added to the solution. The additive may include a buffer such as a phosphate or a citrate, or a mixture thereof. The additive may include potassium iodide (KI). The additive may accelerate the reaction. The additive may accelerate the reaction of the thiocarbamate indicator and the monochloramine. For example, a thiocarbamate indicator may take 10 hours or more to react with monochloramine. The additive may reduce the reaction time and/or accelerate the reaction of the thiocarbamate indicator with monochloramine to approximately 3 minutes. In an embodiment, the pH of the solution may be controlled. Additionally or alternatively, chlorine or chloramine may be added to the solution. In an embodiment, the thiocarbamate indicator in the presence of monochloramine may "turn-on" the fluorescent properties of the thiocarbamate indicator.

In an embodiment, the pH of the solution may be maintained in between 4 and 7, preferably between 5 and 6. The thiocarbamate indicator may be in the concentration range of 5-30 µM. In an embodiment, a buffer may be added. The buffer may be in a concentration range of 10 to 125 mM. In an embodiment, the concentration of phosphate may be in between 10 and 100 mM, and the concentration of citrate may be in between 2 and 20 mM. Saline may be added in the concentration range of 0-50 mM. An approximate range of detection of monochloramine is between 0-5000 ppb or 0-5 ppm.

Figure 5:
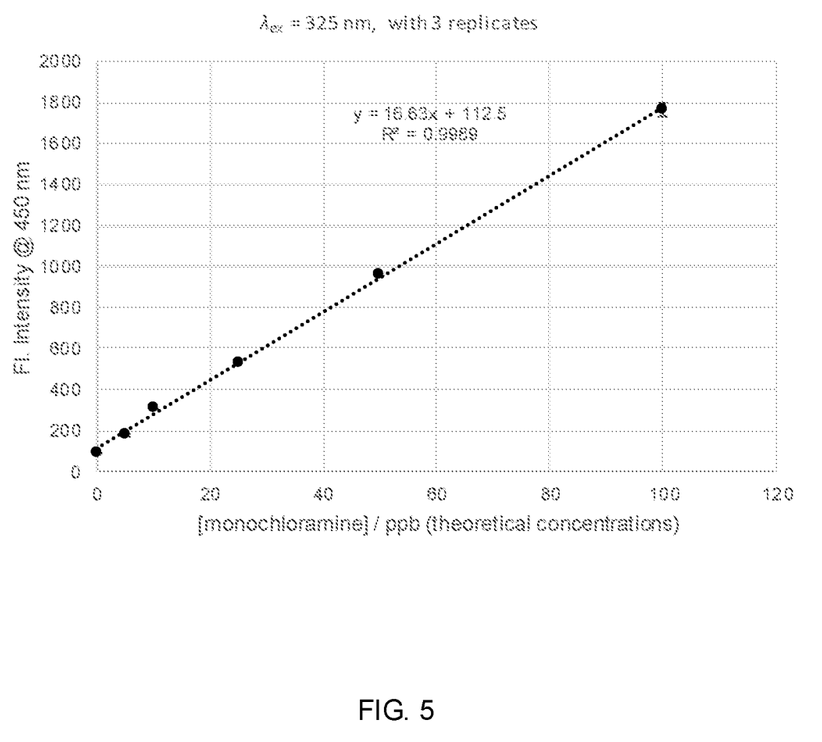
FIG. 5 illustrates an example fluorescence intensity measurement using a thiocarbamate indicator.

At 204, in an embodiment, the system and method may determine if a monochloramine concentration may be determined. In an embodiment, the presence of monochloramine in an aqueous solution may cause an increase in fluorescence intensity of the thiocarbamate indicator. Examples of this increase in fluorescence intensity and dose response curves for a thiocarbamate indicator may be illustrated in FIG. 5. Therefore, the fluorescence intensity, of a solution containing monochloramine may be correlated to the concentration of the monochloramine in the aqueous solution. Fluorescence curves may be generated for a range of monochloramine concentrations, for different thiocarbamate indicators, for any different condition that may affect absorption or fluorescence values (e.g., temperature, sample content, turbidity, viscosity, measurement apparatus, aqueous sample chamber, etc.), or the like.

Alternatively or additionally, monochloramine concentration measurement may be at periodic intervals set by the user or preprogrammed frequencies in the device. Measurement of monochloramine by a device allows for real time data with very little human involvement in the measurement process. Cleaning of the fluorometric chamber may be required at an unspecified time interval. A programmed calibration curve may be entered into the device.

A chamber, vessel, cell, chamber, or the like may contain an aqueous sample, at least one thiocarbamate indicator, and associated reagents such as buffers and/or additives. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, thiocarbamate indicator, and related reagents.

The fluorescent intensity or monochloramine concentration may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels of an analyte. For example, an analyte measuring device may use a relay coupled to an electrically actuated valve, or the like.

At 206, in an embodiment, if a concentration of chlorine cannot be determined, the system may continue to measure monochloramine. Additionally or alternatively, the system may output an alarm, log an event, or the like.

If a concentration of monochloramine can be determined, the system may provide a measurement of monochloramine can concentration at 205. The system may connect to a communication network. The system may alert a user or a network. This alert may occur whether a monochloramine measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a monochloramine concentration reaches a threshold. Alarms or logs may be analyzed in real-time, stored for later use, or any combination thereof.

The various embodiments described herein thus represent a technical improvement to conventional chlorine measurement techniques. Using the techniques as described herein, an embodiment may use a thiocarbamate indicator to measure monochloramine in solution. This is in contrast to DPD chemistry with limitations mentioned above. Such techniques provide a faster and more accurate method for measuring chlorine in an aqueous or liquid solution.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring monochloramine in a sample solution, the method comprising:
    preparing a reaction solution by combining the sample solution, a thiocarbamate derivative, and a buffer such that the reaction solution has a pH between 5 and 6, wherein the sample solution contains an amount of monochloramine;
    measuring a fluorescence intensity of the reaction solution; and
    producing an output of monochloramine concentration in the sample solution based upon the fluorescence intensity.

2. The method of claim 1, further comprising an initial step of preparing the thiocarbamate derivative.

3. The method of claim 2, wherein the thiocarbamate derivative is prepared from a 7-hydroxy coumarin.

4. The method of claim 1, wherein the buffer comprises phosphate.

5. The method of claim 1, wherein the buffer comprises citrate.

6. The method of claim 1, wherein producing an output of monochloramine concentration comprises using fluorescence curves generated from a range of monochloramine concentrations.

7. The method of claim 1, further comprising outputting, using a display, the output of monochloramine concentration.

8. A method for measuring monochloramine in a sample solution, the method comprising:
    preparing a thiocarbamate derivative from a 7-hydroxy coumarin;
    preparing a reaction solution by combining the sample solution, the thiocarbamate derivative, and a buffer comprising phosphate and citrate such that the reaction solution has a pH between 5 and 6, wherein the sample solution contains an amount of monochloramine;
    measuring a fluorescence intensity of the reaction solution; and
    producing an output of monochloramine concentration in the sample solution based upon the fluorescence intensity.

* * * * *